United States Patent [19]

Neel et al.

[11] 4,180,519

[45] Dec. 25, 1979

[54] PROCESS FOR OBTAINING AND PRODUCT ACRYLIC MONOMERS USEFUL IN THE PREPARATION OF CATIONIC FLOCCULANTS

[75] Inventors: Jean Neel; Robert Violland, both of Lyon, France

[73] Assignee: Rhone-Poulenc Industries, Paris, France

[21] Appl. No.: 786,559

[22] Filed: Apr. 11, 1977

Related U.S. Application Data

[63] Continuation of Ser. No. 603,173, Aug. 8, 1975, abandoned.

[30] Foreign Application Priority Data

Aug. 23, 1974 [FR] France ................................ 74 20460

[51] Int. Cl.² .................. C07C 141/10; C07C 93/193
[52] U.S. Cl. ............................... 260/459 A; 526/312; 560/222; 560/218
[58] Field of Search .................. 260/459 A; 560/222, 560/218

[56] References Cited

U.S. PATENT DOCUMENTS

| | | | |
|---|---|---|---|
| 2,677,679 | 5/1954 | Barney | 560/222 |
| 2,702,774 | 2/1955 | Stayner | 260/459 A |
| 2,741,568 | 4/1956 | Hayck | 117/139.5 |
| 2,810,720 | 10/1957 | Lane | 260/459 A |
| 2,854,472 | 9/1958 | Rorig | 260/459 A |
| 2,945,876 | 7/1960 | Klein | 260/456 R |
| 3,336,358 | 8/1967 | McFadden | 560/222 |
| 3,366,663 | 1/1968 | Plischke | 260/459 A |
| 3,661,880 | 5/1972 | Markert et al. | 260/89.5 N |

*Primary Examiner*—Nicky Chan
*Attorney, Agent, or Firm*—Burns, Doane, Swecker & Mathis

[57] ABSTRACT

Process for preparing acrylic monomers comprising reacting, in aqueos medium, amino alkyl esters of (meth) acrylic acid with a quaternizing agent wherein the aqueous solution obtained is washed with a water-insoluble solvent and the solvent thereafter removed. The quaternized monomers prepared are directly polymerizable to high molecular weight homopolymers or copolymers useful as cationic flocculants.

18 Claims, No Drawings

PROCESS FOR OBTAINING AND PRODUCT ACRYLIC MONOMERS USEFUL IN THE PREPARATION OF CATIONIC FLOCCULANTS

This is a continuation of application Ser. No. 603,173 filed Aug. 8, 1975, now abandoned.

The present invention relates to the preparation of acrylic monomers and, more specifically, to the reaction, in aqueous medium, of amino alkyl esters (meth) acrylic acid with quaternizing agents and the polymerization of the obtained product to form high molecular weight acrylate polymers which may be advantageously utilized in numerous applications and are specifically valuable in the field of cationic flocculating agents.

It has long been known to prepare monomers by the quaternization of amino alkylated esters with a halogenated hydracid, an alkyl halide or other quaternization agent capable of forming a salt with the nitrogen of the amino alkylated esters. According to these various prior art processes, the reaction is carried out in aqueous medium or in organic solvent. However, carrying out the reaction in aqueous medium is particularly advantageous because it does not require large amounts of solvent, the manipulation of which is always delicate and expensive and the rate of the quaternization reaction is accelerated in aqueous medium compared to organic solvent processes.

In the field of cationic flocculants, the copolymerization or homopolymerization of monomers in aqueous solution is likewise advantageous. For example, if the monomers are prepared in an organic solvent it is necessary to then dissolve the monomers in water before polymerizing same in order to prepare high molecular weight polymers, in contrast to the preparation in aqueous medium which yields an aqueous solution of the monomer which is directly polymerizable.

Heretofore, the processes for preparing monomers by the quaternization, in aqueous medium, of aminoalkyl esters with a quaternizing agent did not permit the obtention of highly concentrated monomer solutions capable of being directly homopolymerized to obtain high molecular masses without serious disadvantages, such as the resulting homopolymer being in the form of an unusuable gel.

SUMMARY OF THE INVENTION

It is, therefore, a primary object of the present invention to provide a process for preparing concentrated aqueous solutions of quaternized amino alkyl esters of (meth) acrylic monomers while at the same time obviating the problems and disadvantages associated with prior art processes.

It is a further object of the instant invention to provide valuable quaternized amino-acrylate esters which are directly polymerizable in aqueous solution to high molecular weight acrylate homopolymers or copolymerizable with other comonomer to form copolymers.

Still another object of the present invention is to provide cationic flocculating agents derived from polymerized quaternary amino esters of (meth) acrylate monomers.

Other objects, features and advantages of this invention will become more apparent to those skilled in the art from the detailed description of the invention which follows.

DETAILED DESCRIPTION OF THE INVENTION

The present invention relates to a process for preparing acrylate monomers comprising reacting, in an aqueous medium, aminoalkyl esters of (meth) acrylic acid with a quaternization agent wherein the quaternization reaction is effected at a temperature between about 10° and 70° C., and the amino alkyl ester concentration is between about 50 and 90% by weight, thereafter washing the aqueous monomer solution obtained with a water-insoluble solvent and removing the solvent by any conventional solvent removal method.

The monomer which is directly recovered from the quaterization reaction may be polymerized but the resulting high molecular weight homopolymer comprises a water insoluble gel which is, of course, unusable. The organic solvent washing obviates the foregoing by the elimination of those products in the initial quaternized monomer solution which lead to a water-insoluble polymer. The washing also permits the removal of unreacted products from the monomer solution and various other impurities in the reaction products. Thus, it is another advantage of the invention that impure amino alkyl esters of (meth) acrylic acid can be utilized without reducing the performance of the high molecular weight homopolymers ultimately obtained. For example, dialkylaminoalkyl methacrylates are, in general, obtained by transesterification of a lower alkyl methacrylate with a dialkylamino alkanol in the presence of various catalysts and inhibitors. The reaction product, although purified, inherently contains impurities due to the nature of the synethetic reaction, such as hexane, methyl and butyl methacrylate, monomethyl ether of hydroquinone and other non-specific heavy products.

The amino alkylated esters of (meth) acrylic acid used in the invention have the following formula:

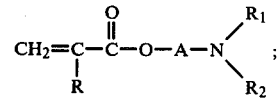

wherein R is H or CH$_3$, A is an alkylene group containing 1 to 3 carbon atoms and, preferably, is an ethylene or isopropylene group and R$_1$ and R$_2$ are the same or different alkyl groups containing 1 to 4 carbon atoms and, preferably, are methyl or ethyl. Dimethylaminoethyl methacrylate, either pure or technical grade, is a particularly preferred reactant.

The quanternization agents utilized for the quaternization of the esters described hereinabove may be any agent conventionally employed or capable of quaternizing the amino nitrogen in the above ester such as, for example, benzyl chloride and alkyl chlorides, including methyl and ethyl chloride, the corresponding bromides and iodides, dimethyl sulfates and sulfites, dimethyl phosphite, and alkylene oxides and the like such as ethylene oxide, propylene oxide and styrene oxide.

The solvents used for washing of the aqueous solution are water-insoluble solvents. Suitable solvents include aliphatic or aromatic hydrocarbons, ethers, esters and halogenated solvents, such as benzene, toluene, hexane, cyclohexane, trichlorethylene, methylchloroform, xylene, heptane, diethylether, ethyl acetate, petroleum ether, butylether, carbon tetrachloride, chloroform 1,2 dichloroethane and monochlorobenzene. Of course, virtually any other water-insoluble organic solvent may be utilized as long as same is readily removable from the system and does not adversely alter the acrylate monomer.

The initial quaternization step is generally carried out as described hereinafter.

The optimum concentration of the ester in water suitable to promote acceptable quaternization is between about 50 and 90% by weight and, preferably, 70 to 80%. The maximum solubility limit of the quarternary ammonium salt in water coincides with an ester concentration approaching 80%.

The reaction is preferably carried out in the presence of an excess of quaternization agent, in comparison with stoichiometric amounts, for obtaining a quantitative reaction and an excess of 10% by weight of the quaternization agent is generally desirable.

The reaction is generally carried out at a temperature between 10° and 70° C., preferably 15° to 30° C. At 30° C., premature polymerization can be minimized and the preferred lower limit of 15° C. is dictated by the slowness of the reaction at this temperature. The regulation of the reaction within these temperature limits may be effectuated during any art recognized method and reactor apparatus.

If the particular quaternization agent selected for the reaction exists in gaseous form or is capable of being gasified, the quaternization agent may advantageously be introduced into the reactor in gaseous form. Before introducing the gaseous quaternization agent, however, inert gases in the reactor should be eliminated by reducing the pressure therein.

Additionally, if the reactor is fed with gaseous quaternization agent, the reaction normally will be concluded under pressure. For instance, when methyl chloride is used, the end of the reaction is carried out under a pressure of about 1.8 bars.

The second step of the process essentially comprises washing the aqueous solution of monomer with a water-insoluble solvent and the washing operation may be effectuated in any conventional manner either after establishing atmospheric pressure conditions in the reactor or by introducing the solvent directly under pressure into the reactor. The ratios of solvent which are used are generally 3 parts by weight of solvent for 10 parts by weight of liquid to be washed although other relative amounts may be used as long as facility of removal is taken into account and effective washing is accomplished. A preferred range for the ratio of solvent to monomer solution is 0.3 to 1.

The next step comprises eliminating the solvent from the aqueous solution by any known means, such as centrifugation or decantation of the mixture recovered after the washing, then drawing off the aqueous phase containing the monomer.

The aqueous solution thus separated may be slightly cloudy owing to the presence of traces of solvent which must be eliminated by evaporation under vacuum, for example, before polymerization. The solution then becomes entirely clear. The foregoing permits, in addition to the elimination of the traces of solvent, concentration of the monomer solution to obtain a saturated solution and to completely degasify same. As a consequence thereof, very hard transparent high molecular weight homopolymers or copolymers are directly obtained by polymerization and the resultant polymers are particularly suitable, after crushing, as flocculating agents.

Suitable comonomers for reaction with acrylate monomer of the invention are acrylic acid and methacrylic acid, alkali metal salts thereof, acrylonitrile, acrylamide and methacylamide.

The following non-limiting examples further illustrate the present invention.

EXAMPLE 1

The quaternization reaction is carried out in an enameled-steel 40 liter reactor, provided with a double jacketed cooling system.

A solution of dimethylaminoethyl methacrylate containing 11,780 parts by weight of methacrylate and 3,890 parts of water is introduced into the reactor corresponding to a 75% solution of the ester.

The reactor pressure is decreased to 400 mm Hg, then methyl chloride is introduced as such a rate that the reaction temperature is kept between 20° and 30° C.

The amount of methyl chloride used is 4,170 parts by weight, corresponding to an excess of 10% relative to the stoichiometric quantity.

When the absorption of methyl chloride begins to slow, the pressure is increased to 1.8 bars and maintained to the end of quaternization. The reaction is completed when the reaction medium is perfectly clear, which is about 3 hours.

The reactor pressure is released, a portion of the excess of methyl chloride being thus eliminated and 5840 parts by weight of benzene are added. Stirring is maintained for 15 minutes and decantion for one hour. The aqueous phase is drawn off, and contains the chloride of ethyltrimethylammonium methacrylate which is kept in an opaque plastic material vessel.

The dry extract of this solution represents 78.7% by weight.

The Brookfield viscosity of this solution is 88 centipoises at 50 t/m and 108 at 100 t/m. The viscosity is measured at 25° C., with a "Brookfield" viscosimeter model RVF 100, Spindle No. 2. The various rotation rates are indicated.

Before polymerizing, the solution obtained is evapoarated under vacuum to eliminate the traces of benzene and, if desired, to concentrate the solution up to monomer saturation.

The evaporation is effected under a vacuum of about 30 to 40 mm of mercury, the liquid being at 55° C., over one hour.

EXAMPLE 2

The quaternization is carried out as described in Example 1 but 5840 parts of hexane instead of benzene are used and the stirring is continued for 45 minutes. The mixture is decanted for one hour and the aqueous phase drawn off.

The remainder of hexane may be eliminated under vacuum of 200 mm at 40° C. for one hour.

The products obtained in Examples 1 and 2 are polymerized by ultra-violet rays in the presence of a photosenzitizer as described in U.S. Pat. application Ser. No. 480,303 which is a continuation in-part of Ser. No. 220,691 filed Jan. 25, 1972, now abandoned, which in turn was a continuation-in-part of Ser. No. 76,603 filed Sept. 29, 1970, now abandoned, and assigned to the assignee herein which disclosure is hereby incorporated by reference. The results set forth in the following table show influence the various stages of the process have on the characteristics of the polymers obtained.

TABLE I

| MONOMER PRODUCT (EXAMPLES) | DRY EXTRACT (Weight %) | PROPERTIES OF THE POLYMER PLATE | BROOKFIELD VISCOSITY OF THE POLYMERIZED PRODUCT IN SOLUTION AT g/l IN WATER | |
|---|---|---|---|---|
| | | | t/mn | centipoises |
| 1 Before washing with benzene | 80.2% | hard, transparent | water-insoluble polymer | |
| 1 After washing with benzene but before evaporation under vacuum | 78.7% | opaque, flexible | 10 | 802 |
| | | | 20 | 564 |
| | | | 50 | 351 |
| | | | 100 | 193 |
| 1 After evaporation under vacuum | 82.1% | transparent very hard, crispy | 10 | 1490 |
| | | | 20 | 1060 |
| | | | 50 | 616 |
| | | | 100 | 419 |
| 1 After evaporation, the concentration of the solution being adjusted to 78.7% with water | 78.7% | transparent hard | 10 | 1145 |
| | | | 20 | 861 |
| | | | 50 | 529 |
| | | | 100 | 368 |
| 2 After washing with hexane but before evaporation under vacuum | 79.6% | opaque hard | 10 | 1380 |
| | | | 20 | 830 |
| | | | 50 | 496 |
| | | | 100 | 342 |
| 2 After evaporation under vacuum | 80.1% | transparent very hard | 10 | 1400 |
| | | | 20 | 892 |
| | | | 50 | 515 |
| | | | 100 | 365.6 |

Summarizing the foregoing results, it is apparent that:

(1) If the washing of the reaction product with an organic solvent is omitted, the resulting polymer is insoluble in water.

(2) After washing with benzene, the reaction product, even after prolonged decantation, but before evaporation under vacuum, contains about 2 to 3% of residual benzene which considerably reduces the viscosity of the solution at 5 g/l in water and the polymer plate is too flexible to be satisfactorily crushed. The obtained polymer contains, moreover, a certain amount of non-polymerized monomer (1.035%). The evaporation under vacuum of the aqueous phase eliminates the residual benzene and avoids these disadvantages. The preceding is illustrated in the table by means of the viscosities, corresponding to a dry extract of 78.7% and which are given for products both after washing with benzene but before evaporation under vacuum (traces of benzene are present) and after evaporation under vacuum, the concentration of the solution being 78.8% with water (no trace of benzene is present).

(3) After washing with hexane and decantation (Example 2), the reaction product contains much less residual solvent and, as a consequence thereof, the hardness of the plate and the viscosity of the polymer in solution at 5 g/l in water are not seriously affected.

While the invention has been described and pointed out with reference to certain preferred embodiments thereof, those skilled in the art will appreciate that various changes and modifications and substitutions can be made without departing from the spirit of the invention. It is intended therefore, that the invention be limited only by the scope of the claims which follow.

What is claimed is:

1. A process for preparing a highly concentrated aqueous quaternary acrylic ester monomer solution which is directly polymerizable to form hard, transparent, water-soluble, high molecular weight cationic acrylic polymers and which comprises a major content of a salt of a monomeric compound of formula I

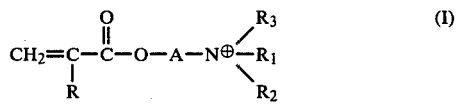

wherein R represents hydrogen or methyl, A represents an alkylene group containing 1 to 3 carbon atoms, $R_1$ and $R_2$ are the same or different and each represents an alkyl group containing 1 to 4 carbon atoms, and $R_3$ represents a lower alkyl or benzyl group, said process comprising the steps of:

(a) reacting an aqueous mixture containing about 50 to about 90% of a compound of formula II

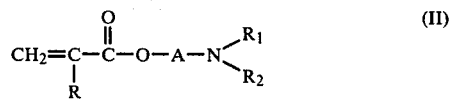

wherein $R_1$, $R_2$, R and A are as defined above, with a quaternizing agent of formula $R_3X$, wherein $R_3$ is as defined above and X is halogen or the $-CH_3SO_4$ group at a temperature of between about 10° and about 70° C. whereby a crude aqueous solution of a salt of a compound of formula I is obtained;

(b) treating said crude aqueous solution with a water-insoluble solvent in order to obtain a mixture comprising a purified aqueous phase containing the salt of the compound of formula I and being substantially free of impurities of unreacted starting materials and of impurities which induce the formation of water-insoluble polymers, and an organic phase containing the water-insoluble solvent and said impurities;

(c) separating the organic base of said mixture from the purified aqueous phase; and, (d) further purifying said purified aqueous phase and recovering therefrom a highly concentrated clear aqueous solution of the salt of the compound of formula I sufficiently free of said impurities and organic solvents said aqueous solution being directly polymerizable into a hard, transparent, water-soluble, high molecular weight cationic acrylic polymer.

2. The process as defined in claim 1, wherein $R_3$ is methyl.

3. The process as defined in claim 1, wherein A is ethylene and $R_1$ and $R_2$ are each methyl.

4. The process as defined in claim 1, wherein said compound of formula II comprises dimetylaminoethyl methacrylate.

5. The process as defined in claim 1, wherein the quaternizing agent $R_3X$ is an alkyl halide.

6. The process as defined in claim 2, wherein the quaternzing agent is a methyl halide.

7. The process as defined in claim 5, wherein step (a) comprises introducing said quaternization agent in gaseous form.

8. The process as defined in claim 1, wherein in step (a) the amount of said quaternization agent in said reaction comprises an excess of 10% by weight relative to the stoichiometric amounts of said agent and said compound of formula II.

9. The process as defined in claim 1, wherein in step (a) said temperature is between about 15° C. and about 30° C.

10. The process as defined in claim 1, wherein in step (a) the aqueous mixture contains between about 70% to about 80% of the compound of formula II.

11. The process as defined in claim 1, wherein step (b) comprises treating the crude aqueous solution with three parts of solvent per ten parts of said aqueous solution.

12. The process as defined in claim 1, wherein said water-insoluble organic solvent is selected from the group consisting of aliphatic hydrocarbons, aromatic hydrocarbons, ethers, esters and halogenated hydrocarbons.

13. The process as defined in claim 12, wherein the solvent is an aliphatic or aromatic hydrocarbon.

14. The process as defined in claim 13, wherein said water-insoluble solvent is selected from the group consisting of benzene, toluene, hexane, cyclohexane, petrolether, trichloroethylene, methylchloroform, xylene, heptane, diethylether, butyl ether, ethyl acetate, carbon tetrachloride, chloroform 1,2-dichloroethane, and monochlorobenzene.

15. The process as defined in claim 13, wherein the solvent is benzene or hexane.

16. The process as defined in claim 1, wherein the separating step (c) comprises decantation or centrifugation of said mixture.

17. The process as defined in claim 1, wherein step (d) comprises the step of evaporating a portion of the purified aqueous phase, whereby any traces of the organic solvent are removed.

18. The process as defined in claim 17, which comprises evaporating a portion sufficient to obtain a saturated solution of the salt of the compound of formula I.

* * * * *

UNITED STATES PATENT AND TRADEMARK OFFICE
CERTIFICATE OF CORRECTION

PATENT NO. : 4,180,519

DATED : December 25, 1979

INVENTOR(S) : Jean Neel and Robert Violland

It is certified that error appears in the above-identified patent and that said Letters Patent are hereby corrected as shown below:

Column 4, line 4, correct "methacylamide" to read

-- methacrylamide --;

Column 4, line 29, replace "5840" with -- 5,840 --; and

Column 6, lines 58-59, the formula split between the end of line 58 and the beginning of line 59 should be on one line as -- $-CH_3SO_4$ --.

Signed and Sealed this

Seventeenth Day of June 1980

[SEAL]

Attest:

SIDNEY A. DIAMOND

Attesting Officer

Commissioner of Patents and Trademarks